United States Patent
Weinberg et al.

(10) Patent No.: US 9,694,196 B2
(45) Date of Patent: Jul. 4, 2017

(54) SYSTEM, METHOD AND EQUIPMENT FOR IMPLEMENTING TEMPORARY DIAMAGNETIC PROPULSIVE FOCUSING EFFECT WITH TRANSIENT APPLIED MAGNETIC FIELD PULSES

(71) Applicant: WEINBERG MEDICAL PHYSICS LLC, Bethesda, MD (US)

(72) Inventors: Irving N. Weinberg, Bethesda, MD (US); Aleksandar Nelson Nacev, Bethesda, MD (US); Pavel Stepanov, North Potomac, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 303 days.

(21) Appl. No.: 14/182,488

(22) Filed: Feb. 18, 2014

(65) Prior Publication Data
US 2014/0309479 A1 Oct. 16, 2014

Related U.S. Application Data

(60) Provisional application No. 61/810,436, filed on Apr. 10, 2013.

(51) Int. Cl.
*A61N 2/00* (2006.01)
*A61N 2/02* (2006.01)
*G01R 33/12* (2006.01)
*A61K 41/00* (2006.01)
*A61M 37/00* (2006.01)
*A61N 5/10* (2006.01)

(52) U.S. Cl.
CPC ............. *A61N 2/02* (2013.01); *A61K 41/0028* (2013.01); *G01R 33/1276* (2013.01); *A61M 37/00* (2013.01); *A61N 2005/1098* (2013.01)

(58) Field of Classification Search
CPC ......... H04B 1/3888; H04B 2001/3894; H04M 1/0249; H04M 1/0262; H04M 1/0266; H04M 1/18; H04M 1/23; H04M 1/236; A61N 2/02; A61N 2005/1098; A61K 41/0028; G01R 33/1276; A61M 37/00
USPC ..................... 335/216; 600/12; 198/617, 619
See application file for complete search history.

(56) References Cited

U.S. PATENT DOCUMENTS

| | | | | |
|---|---|---|---|---|
| 6,628,042 B2 * | 9/2003 | Tomohiro | ............. | H01L 41/257 264/435 |
| 2003/0067235 A1 * | 4/2003 | Vazquez | ............... | B64C 39/001 310/152 |

OTHER PUBLICATIONS

Earnshaw, "On the Nature of the Molecular Forces Which Regulate the Luminiferous Ether", Transactions of Cambridge Philosophical Society, vol. 7, (1839), pp. 97-112.

Aleksander Nacev et al., "Towards Control of Magnetic Fluids in Patients", Directing Therapeutic Nanoparticles to Disease Locations, IEEE Control Systems Magazine, vol. 32, (Jun. 2012), pp. 32-74.

M. D. Simon et al., "Diamagnetic Levitation: Flying Frogs and Floating Magnets (Invited)", Journal of Applied Physics, vol. 87, No. 9, (May 2000), pp. 6200-6204.

* cited by examiner

*Primary Examiner* — Bernard Rojas
(74) *Attorney, Agent, or Firm* — Barnes & Thornburg LLP

(57) ABSTRACT

An apparatus and method are utilized to transiently implement diamagnetic behavior in both permanently and transiently magnetized particles.

19 Claims, 4 Drawing Sheets

SYSTEM, METHOD AND EQUIPMENT FOR IMPLEMENTING TEMPORARY DIAMAGNETIC PROPULSIVE FOCUSING EFFECT WITH TRANSIENT APPLIED MAGNETIC FIELD PULSES

CROSS REFERENCE

This application relies for priority on U.S. Provisional Application No. 61/810,436 filed Apr. 10, 2013, and entitled "Neuroparticle", the contents of which are incorporated herein by reference.

FIELD

The invention has application to the focused transport of magnetizable particles, as may be used to deliver medical therapy to an internal tissue.

BACKGROUND

In 1842, Samuel Earnshaw showed (in the article "On the nature of the molecular forces which regulate the constitution of the luminiferous ether" published by the journal Transactions of the Cambridge Philosophical Society, Vol. 7, pages 97-112), that magnetic "instability cannot be removed by [any] arrangement" of magnets. In his published proof, Earnshaw examined the potential energy of a single particle being attracted by many others. He showed that the energy field for this particle must always be the shape of a peak or at best a hyperboloid (a saddle), so that motion of a particle in this field will always be unstable. Therefore any arrangement of magnets to attempt to create a focal point in space will be unstable. This instability is of importance to physicians attempting to deliver drugs or other therapies with magnetizable nanoparticles as carriers focused to tumors or to other tissues of interest.

Although originally proved for particles that were permanently magnetized, Earnshaw's result also applies to temporarily magnetizable (e.g., ferromagnetic, ferrimagnetic, paramagnetic, super-paramagnetic) particles immersed in a magnetic field. This proof is recited in the article by A. Nacev et al published in the journal IEEE Control Systems Magazine, Vol. 32, issue 3, and entitled "Towards Control of Magnetic Fluids in Patients: Directing Therapeutic Nanoparticles to Disease Locations." Specifically, equation S2 of the article shows that the second derivative of the potential energy (i.e., the Laplacian) is negative if the magnetic force on a particle in a magnetic field is in the same direction as the increasing gradient of that field. This negative second derivative implies that at best the particles may reside in an energy saddle, with no stable well that is able to focus or confine the particles. As a result, it is not conventionally possible to concentrate magnetizable particles in an interior volume solely through the use of magnetic fields. The mathematical proof, discussed in the article by A. Nacev et al, illustrates a potential loop-hole in Earnshaw's theorem: if the particle was diamagnetic (i.e., if the magnetic force was in the opposite direction from an increasing magnetic gradient), an energy well could be constructed of externally-applied magnetic fields that could be used to focus the diamagnetic particles at a distance away from the magnetic field source.

The force on a particle immersed in a magnetic field is approximately proportional to the particle's susceptibility. Unfortunately, most diamagnetic materials have very small magnetic susceptibility (and hence experience lower magnetic forces), requiring extremely strong magnetic fields for particle manipulation. M. D. Simon and A. K. Geim, in their 2000 article in the Journal of Applied Physics (Vol. 87, number 9, pages 6200-6204) entitled "Diamagnetic levitation: Flying frogs and floating magnets", point out that a 12-Tesla magnet is required for droplets of water (or frogs containing water) to overcome gravity. Water has a susceptibility of about $10^{-5}$ in CGS units of $cm^3$ $mol^{-1}$. Ferromagnetic and paramagnetic materials have much higher susceptibilities. Nickel oxides, for example, have susceptibilities on the order of 10,000 $cm^3$ $mol^{-1}$ (i.e., nine orders of magnitude larger).

SUMMARY

In disclosed embodiments, an apparatus and method are utilized which transiently implement diamagnetic behavior in both permanently and transiently magnetized particles.

BRIEF DESCRIPTION OF THE FIGURES

The invention will now be described in connection with the drawings appended hereto, in which.

DETAILED DESCRIPTION

Figure 1:
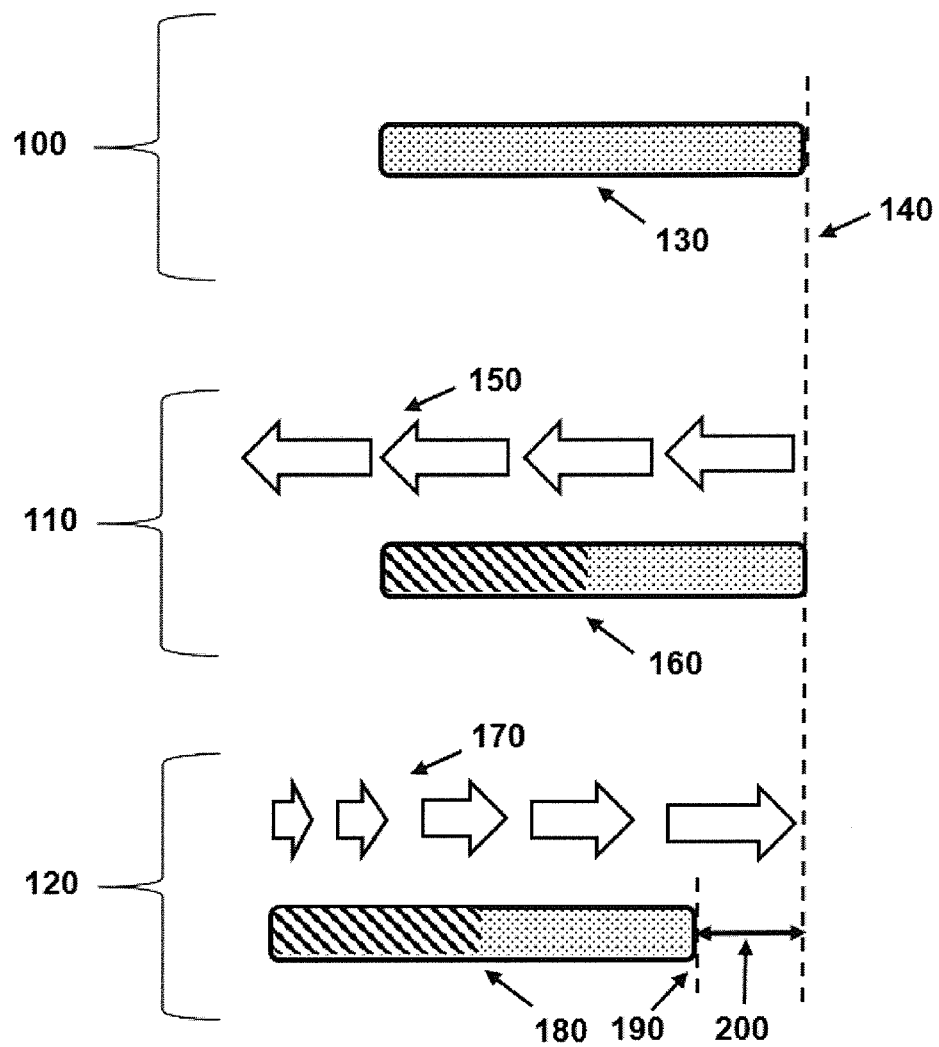
FIG. 1 illustrates one example of a methodology provided in accordance with the disclosed embodiments.

The method can be summarized as follows, and as illustrated in FIG. 1. FIG. 1 represents three successive operations of the disclosed embodiments, shown as 100, 110, and 120. The duration of time between operations 100 and 110 is sufficient to polarize a particle 130. The duration of time between operations 110 and 120 is less than the time it takes to polarize or depolarize a particle 130.

It should be understood that operations 100, 110, and 120 may be repeated many times, and in different directions. In the first operation 100 of the method, one or more particles 130 that are made of magnetizable material (e.g., paramagnetic) is located at a position 140. For illustrative purposes, particle 130 is shown in FIG. 1 as having no net magnetization at the time of this operation 100. In practice, the present invention envisages a case in which particle 130 may have some net magnetization left over from a prior operation. For illustrative purposes, particle 130 is represented as an oblong structure, which is favorable in terms of operation of the invention because a long shape confers a large moment of angular inertia. However, particle 130 may have a different shape.

In the next operation 110, a relatively uniform magnetic field 150 has been applied to the particle, so that the particle is now polarized according to the direction of the relatively uniform magnetic field 150. The newly polarized state of the particle is represented by shaded particle 160. Since particle 160 is in a relatively uniform field, particle 160 may rotate but does not translate from its initial position 140. In an alternative embodiment, particle 160 is a magnetic particle and does not require polarization but is simply oriented by the relatively uniform magnetic field 150.

In the next operation 120, a magnetic gradient 170 with polarity in the opposite direction from 150 is applied to the particle. Since the switching time from operation 110 to 120 is less than the time it would take the particle (now denoted as 180) to depolarize, the particle is accelerated by the magnetic gradient 170 in a linear direction that is opposite to the direction of increasing gradient strength. As a result of this acceleration, particle 180 is displaced from its equilibrium position 140 to a new position 190, with a displacement given by distance 200.

Operation 120 lasts for a duration that is less than the time that it would take for particle 180 to turn around and/or to completely depolarize. If the angular moment of inertia is high, it will take longer for particle 180 to turn around than if the moment of inertia is low. Both magnetic and structural interactions with nearby particles can effectively add to or subtract from the moment of inertia of particle 180.

As a result of successive applications of operations 100, 110, and 120, particles 180 are moved in the direction of decreasing gradient strength. It should be noted that unlike typical paramagnetic motion, the motion of the particle is in the direction of decreasing gradient strength. In practice, this action has the effect of temporarily conferring diamagnetic properties upon a particle that has high magnetic permeability.

It should be understood that the application of a relatively uniform magnetic field may be used to orient a magnetic particle so that it may be subsequently pushed with a subsequent gradient magnetic field. In this way, the present invention may be used to propel ferromagnetic or magnetic particles.

It should be understood that additional magnetic field pulses may be applied to remove magnetic polarization from a particle (i.e., in a de-gaussing action), so as to prevent agglomeration of the particles or other deleterious effects.

It should be understood that the magnetic strength of an electromagnetic coil as envisaged in the present invention activated by a voltage or power source may be substantially increased by cooling the electromagnetic coil, for example to liquid nitrogen temperatures.

Although the method is above explained as using separate polarizing and gradient magnetic pulses, it should be understood that the method includes the application of a polarizing field that may continue or diminish during the application of the transient magnetic gradient field pulse, or of a gradient field that may continue or diminish during the application of a transient gradient field pulse. For the purposes of explanation, the magnetic fields are denoted as "transient". It should be understood that the terms "transient" and "pulse" includes the case so where at least one portion of the polarizing magnetic field or gradient field magnetic field is transient. For example, a continuously operating polarizing magnetic field with a temporarily elevated magnitude would be included under the term "transient", since at least one portion of the polarizing magnetic field is temporary.

It should be understood that although the disclosed embodiments are described in application to ferromagnetic, ferrimagnetic, paramagnetic, super-paramagnetic, and magnetic particles, it will also be of use to particles that contain some or all of the properties of ferromagnetic, ferrimagnetic, paramagnetic, super-paramagnetic, and magnetic particles. As an example, the particle may be multi-ferroic, or may have internal logic elements that determine its magnetic properties, or the particle's magnetic properties may be influenced by externally-applied or internal electromagnetic or acoustic fields.

Figure 2:
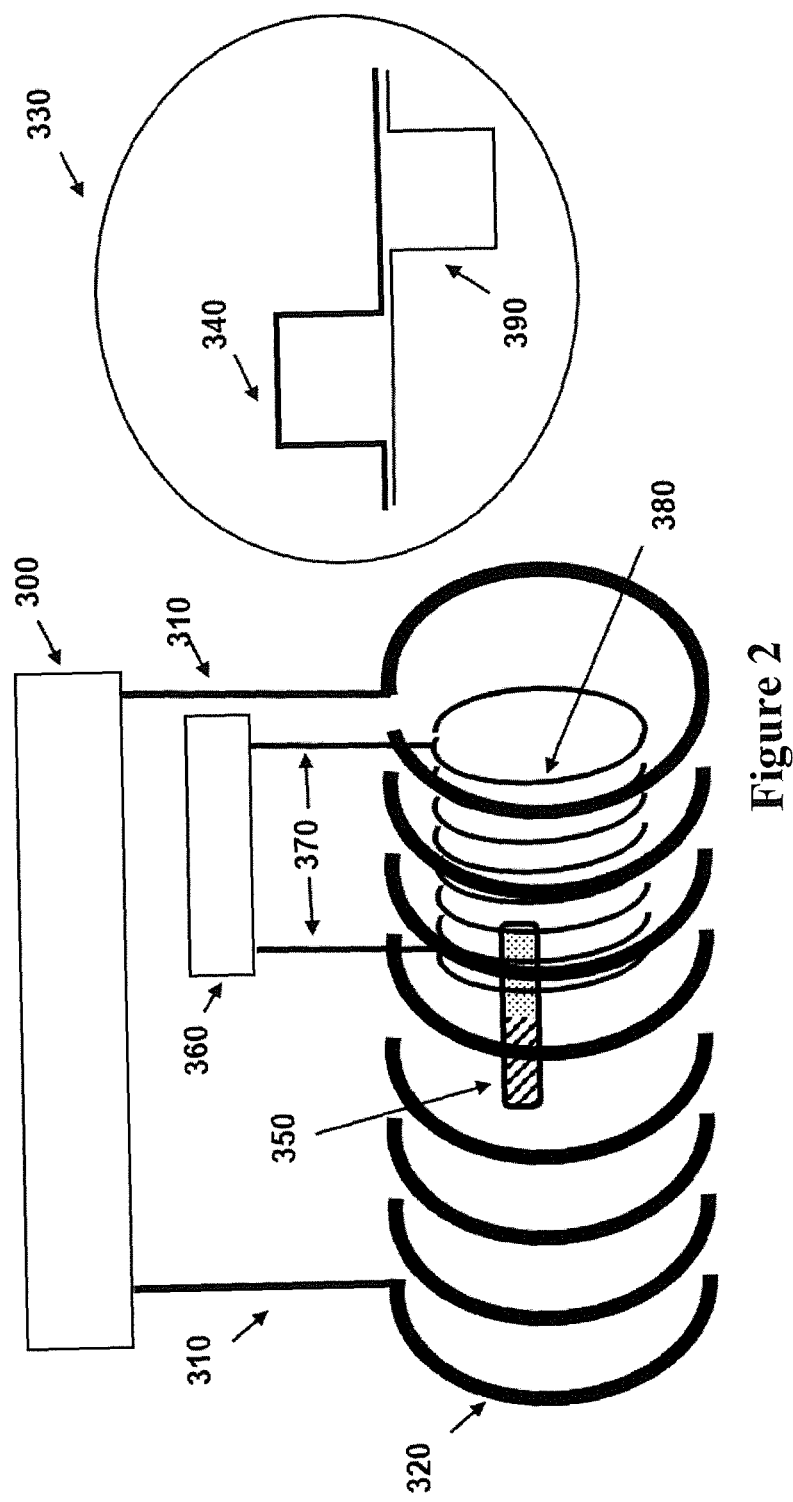
FIG. 2 represents a one-dimensional example of the invented apparatus used to implement the method shown in FIG. 1.

FIG. 2 represents a one-dimensional example of the invented apparatus used to implement the method shown in FIG. 1. In FIG. 2, pulse generator 300 sends a first current pulse through cables 310 to the polarizing coil 320. A representation 340 of the current pulse (as might be seen on an oscilloscope) from generator 300 is shown as an inset 330. This first current pulse represents the second operation 110 of FIG. 1. As in operation 110, particle 350 becomes polarized and/or oriented by the magnetic field produced by polarizing coil 320. In an embodiment of the present invention, the magnetic field produced by polarizing coil 320 is relatively uniform (e.g., 10% over the field of action). In an alternative embodiment, the magnetic field produced by polarizing coil 320 is not uniform. In an embodiment of the present invention, the magnetic field is produced by a single polarizing coil 320. In an alternative embodiment, the polarizing magnetic field is produced by a combination of coils and/or permanent magnets. A short time later (i.e., before the polarization of particle 350 has decayed substantially), pulse generator 360 sends a second current pulse through cables 370 to a gradient coil 380, which through the establishment of a magnetic gradient field exerts a force on the previously-polarized particle 350. In an embodiment of the present invention, the magnetic gradient field is produced by a single gradient coil 380. In an alternative embodiment, the gradient magnetic field is produced by a combination of coils and/or permanent magnets. A representation 390 of the second current pulse (as might be seen on an oscilloscope) from generator 360 is shown in inset 330. It should be understood that the pulse sequence shown in inset 330 can be repeated and modified.

Figure 3:
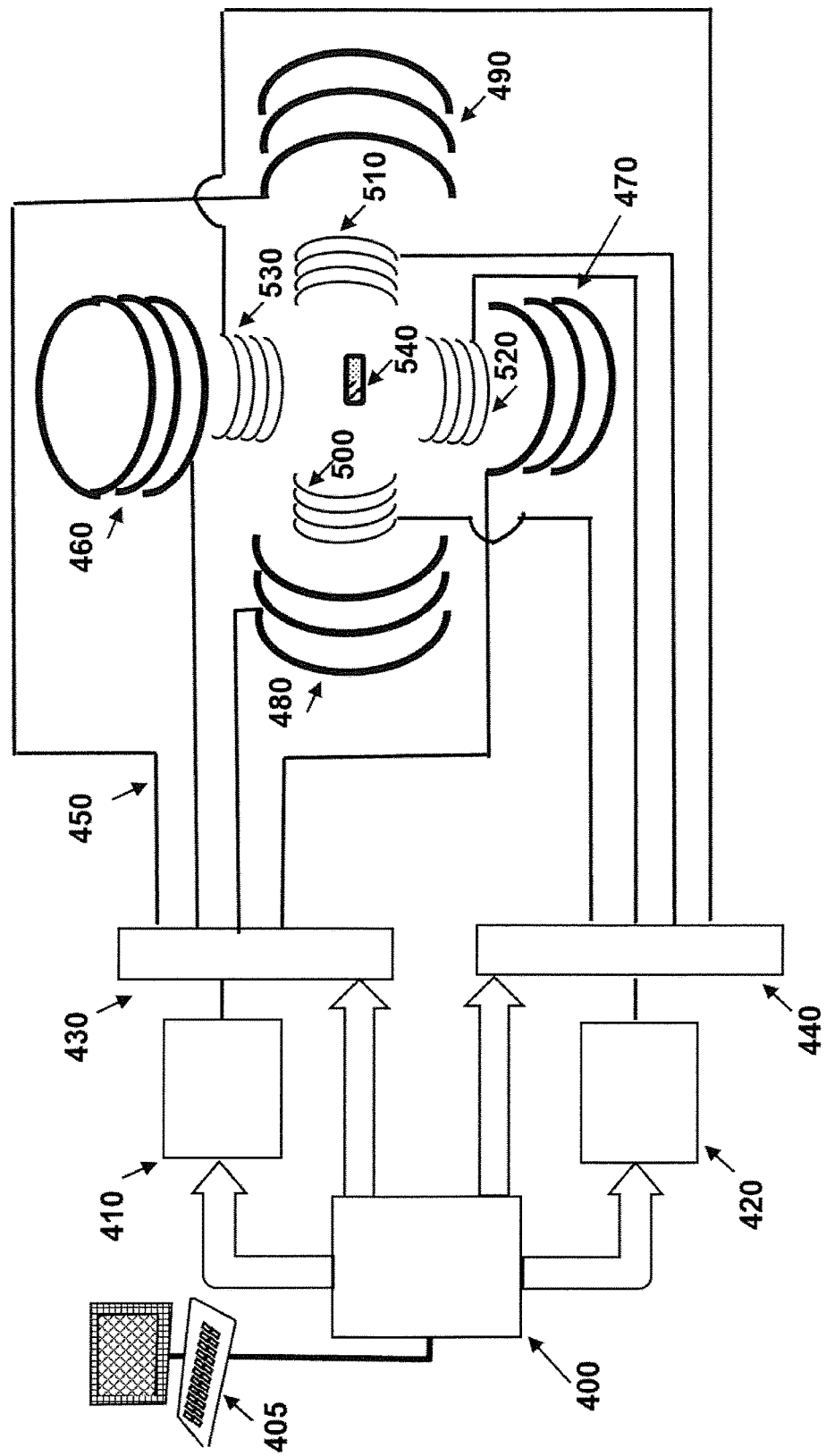
FIG. 3 represents a two-dimensional example of the invented apparatus used to implement the method shown in FIG. 1.

FIG. 3 represents a two-dimensional example of the invented apparatus used to implement the method shown in FIG. 1. In FIG. 3, computer or other electronic system 400 (shown with exemplary input/output devices 405) controls polarizing pulse generator 410 and gradient pulse generator 420, and also controls polarizing pulse multiplexer 430 and gradient pulse multiplexer 440. It should be understood that multiplexers 430 and 440 may contain high-current relays. For simplicity, only one representative wire (e.g., 450) is shown emanating from the multiplexers to each of the coils generating magnetic fields. It should be understood that each coil will generally require at least two wires to be activated. Magnetically-polarizing coils include polarizing pair 460 and 470, which polarize a particle in a different direction than polarizing pair 480 and 490. It should be understood that the polarizing coils may orient the particle in addition to, or instead of, polarizing the particle. Magnetic gradient-producing coils include gradient coils 500, 510, 520, and 530, which when operated independently immerse a particle in a different magnetic gradient direction. In the present embodiment only one gradient coil (500, 510, 520, or 530) is active at a time, but in alternative embodiments multiple gradient-producing coils may be active simultaneously. It should be understood that the coils in each direction may be activated in series instead of separately, if necessary. It should be understood that additional coils and/or permanent magnets may be added, for example to cover diagonal directions and/or to extend the apparatus to cover the three-dimensional case. A particle 540 is shown in the center of the apparatus.

In typical operation of the apparatus shown in FIG. 3, computer 400 instructs that a set of polarizing coils (e.g., horizontal coils 480 and 490) is supplied by a current from the pulse generator 410 and multiplexer 430. The resulting relatively uniform magnetic field around exemplary particle 540 polarizes it and orients it (e.g., horizontally in FIG. 3). A short time later ((i.e., before the polarization of particle 540 has decayed substantially), computer 400 instructs that a gradient producing coil (e.g., horizontal coil 500) is supplied by a current from the pulse generator 420 and multiplexer 440. The resulting magnetic gradient around exemplary particle 540 propels it horizontally.

The magnetic polarization and gradient coils may be employed to image particles or the environment in which the particles reside. For example, a source and detector of radiofrequency energy may be added that can interrogate and localize protons or atomic nuclei (as in nuclear magnetic resonance imaging) or electrons (as in electron paramagnetic resonance imaging) or particles (as in magnetic particle imaging).

As disclosed in the prior invention by I. N. Weinberg, entitled "Neuroparticle", U.S. patent application Ser. No. 61/810,436, particles may be localized via changing magnetic gradients. In an embodiment of the present invention, pulse sequences responsible for imaging are interleaved with the pulse sequences responsible for particle propulsion in order to implement image-guided particle delivery. Since the particles may carry payloads, or deliver energy (e.g., electrical or heat), or potentiate therapy from other sources (e.g., by increasing the destructive power of an externally-applied beam of radiation), the interleaving sequences can implement image-guide therapy.

It should be understood that particles may be asymmetric in shape, of varying sizes and magnetic composition. It should be understood that the term "particles" may apply to agglomerations (i.e., clumps) or assemblies of particles, and of particles of sizes varying from atomic to macroscopic (e.g., centimeters). For asymmetric particles or assemblies of particles, the moment of inertia of the particles will be different than that of individual particles (and hence, the time in which the particle will remain oriented and/or polarized after application of the polarizing magnetic pulses).

It should be understood that magnetic particles may push, displace, turn, or otherwise affect nearby non-magnetic particles, structures, or tissues.

It should be understood that coils may be actuated asymmetrically with varying current so that the magnitude of the magnetic fields need not be symmetric with respect to the center of the distance between the coils.

It should be understood that although repulsive (e.g., diamagnetic) behavior is emphasized in this invention because of their novelty, the same disclosed embodiments can also readily implement attractive forces as needed in order to manipulate one or more magnetizable particles, for example by setting up appropriate magnetic gradient fields with or without pre-polarizing pulses.

It should be understood that the recursive application of diamagnetic propulsive pulse sequences as described above can focus particles.

Figure 4:
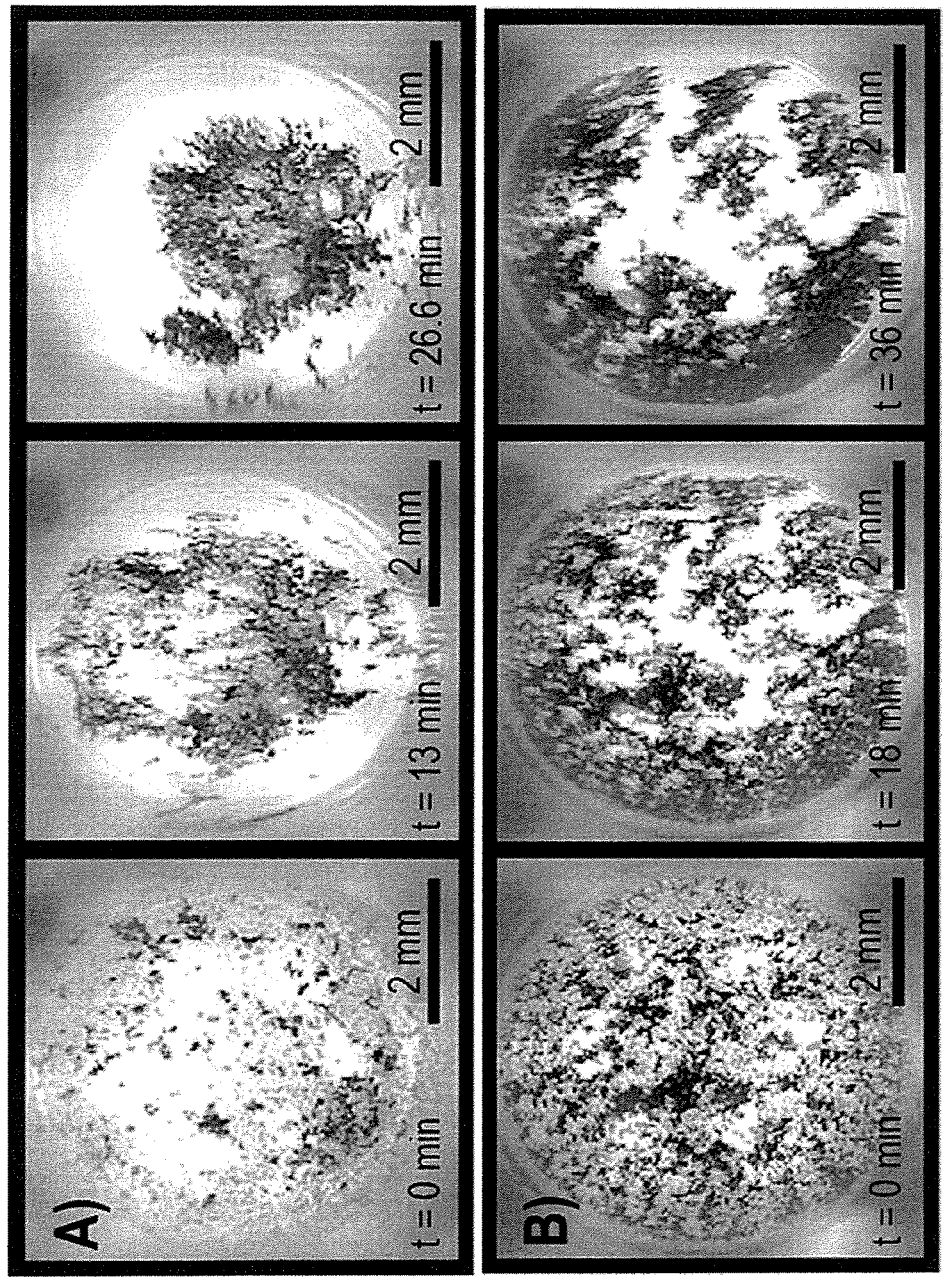
FIG. 4 is an illustrative diagram illustrating that no focusing occurred when gradient pulses were applied in the absence of polarizing pulses.

FIG. 4 illustrates the effect of sequential application of polarizing and gradient pulses. The top three panels in FIG. 4(a) show focusing of a set of particles through the use of both polarizing and gradient pulses. The bottom three panels of FIG. 4(b) show that no focusing occurred when gradient pulses were applied in the absence of polarizing pulses.

It should be understood that disclosed embodiments may be implemented at least in part using or under the direction of a computer which may include one or more processors configured to run software to both control operations disclosed there. Likewise, the computer 400 may be configured to run algorithms that output data pertaining to the operations and/or one or more graphical or image representations pertaining to the operations to output equipment 405. That output equipment may include, for example, one or more computer screens, printers, etc. provided to enable review of that output data by medical and diagnostic personnel. It should be understood that the link between such a processor(s) and the output equipment may be a wired link, a wireless transmission medium or any other direct or indirect connection that enables transfer of data.

Likewise, such a processor(s) may be further configured to output the image data and/or one or more graphical or image representations of the data to memory for storage and further analysis or reference at a later date. Further, the software code, instructions and algorithms utilized by the processor(s) may be stored in the memory. Accordingly, memory may include any type of known memory device including any mechanism for storing computer executable instructions and data used by a processor. Further, the memory may be implemented with any combination of read only memory modules or random access memory modules, optionally including both volatile and nonvolatile memory. Alternatively, some or all of the device computer executable instructions may be embodied in hardware or firmware (not illustrated).

Further, it should be appreciated that, although not illustrated, the equipment may include one or more user interfaces that may include display screens, one or more keyboards, and other types of user interface equipment.

As noted above, there are numerous variations and equivalents of the present invention that should be appreciated by those skilled in the art. The present invention is intended to encompass those equivalents and variations.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

Other aspects of the present invention should be apparent to those skilled in the art based on the discussion provided herein.

What is claimed is:

1. A method of eliciting diamagnetic behavior in at least one ferromagnetic, paramagnetic, super-paramagnetic, or other magnetizable or magnetic particles, the method comprising:
applying at least one transient magnetic gradient field to at least one particle,
wherein the at least one particle has been polarized and/or oriented through the application of a magnetic field in a direction that is opposing the direction of the transient magnetic gradient field, and
wherein the particle is translated in space as a result of the force applied by the at least one transient magnetic gradient field.

2. The method of claim 1, wherein onset and duration of application of the at least one transient magnetic gradient field is less than the time required for the at least one particle to completely depolarize.

3. The method of claim 1, wherein onset and duration of application of the at least one transient magnetic gradient field is less than the time required for the at least one particle to re-orient itself.

4. The method of claim 1, wherein the at least one particle travels towards the direction of decreasing magnetic gradient strength.

5. The method of claim 1, wherein the effect of repeated application of diamagnetic behavior is used to concentrate particles in space.

6. The method of claim 1, wherein the at least one particle is loaded with a chemical.

7. The method of claim 1, wherein the at least one particle delivers therapy or potentiates therapy.

8. The method of claim 1, wherein intervening magnetic pulses provide imaging guidance for particle motion.

9. The method of claim 1, wherein degaussing magnetic pulses de-clump assemblies of particles.

10. An apparatus of at least one electromagnetic coil and/or permanent magnet controlled by a computer and/or electronic system, in which the apparatus provides at least one transient magnetic gradient field to at least one ferromagnetic, paramagnetic, super-paramagnetic, or other magnetizable or magnetic particle, where the at least one particle has been polarized and/or oriented through the application of a magnetic field in a direction that is opposing the direction of the transient magnetic gradient field, and wherein the particle is translated in space as a result of the force applied by the at least one transient magnetic gradient field.

11. The apparatus of claim 10, wherein the onset and duration of application of the at least one transient magnetic gradient field is less than the time required for the at least one particle to completely depolarize.

12. The apparatus of claim 10, wherein the onset and duration of application of the at least pulsed magnetic gradient field is less than the time required for the at least one particle to re-orient itself.

13. The apparatus of claim 10, wherein the at least one particle travels towards the direction of decreasing magnetic gradient strength.

14. The apparatus of claim 10, wherein the effect of repeated use of the apparatus concentrates particles in space.

15. The apparatus of claim 10, wherein the at least one particle is loaded with a chemical.

16. The apparatus of claim 10, wherein the at least one particle delivers therapy or potentiates therapy.

17. The apparatus of claim 10, wherein intervening magnetic pulses provide imaging guidance for particle motion.

18. The apparatus of claim 10, wherein at least one electromagnetic coil is cooled in order to increase magnetic field strength.

19. The apparatus of claim 10, wherein the apparatus delivers degaussing magnetic pulses in order to de-clump assemblies of particles.

* * * * *

UNITED STATES PATENT AND TRADEMARK OFFICE
CERTIFICATE OF CORRECTION

PATENT NO. : 9,694,196 B2  
APPLICATION NO. : 14/182488  
DATED : July 4, 2017  
INVENTOR(S) : Weinberg et al.

Page 1 of 1

It is certified that error appears in the above-identified patent and that said Letters Patent is hereby corrected as shown below:

On the Title Page

Item (72) Inventor is corrected to read:
-- Irving N. Weinberg, Bethesda (MD);
Aleksandar Nelson Nacev, Bethesda (MD) --.

Signed and Sealed this
Nineteenth Day of March, 2019

Andrei Iancu
*Director of the United States Patent and Trademark Office*